United States Patent [19]

Watson et al.

[11] Patent Number: 4,466,904
[45] Date of Patent: Aug. 21, 1984

[54] POLYMERIZATION CO-INHIBITORS FOR VINYL AROMATIC COMPOUNDS

[75] Inventors: James M. Watson; James R. Butler, both of Big Spring; Karen A. Mikkelson, Lubbock, all of Tex.

[73] Assignee: Cosden Technology, Inc., Dallas, Tex.

[21] Appl. No.: 456,876

[22] Filed: Jan. 10, 1983

[51] Int. Cl.$^3$ .......................... C09K 15/26; C08F 2/38
[52] U.S. Cl. ...................................... 252/402; 526/83; 526/84; 526/85
[58] Field of Search ...................... 252/402; 526/83–85

[56] References Cited

U.S. PATENT DOCUMENTS

| | | | |
|---|---|---|---|
| 1,950,438 | 2/1934 | Carothers et al. | 526/85 |
| 2,225,471 | 12/1940 | Foord | 526/84 |
| 2,576,009 | 11/1951 | Goertz et al. | 526/83 |
| 3,265,659 | 8/1966 | Kobayashi et al. | 252/403 |
| 4,343,956 | 8/1982 | Jackisch | 252/403 |

OTHER PUBLICATIONS

Murphy et al., Industrial & Engineering Chemistry, vol. 42 (1950), pp. 2479–2489.

*Primary Examiner*—Christine M. Nucker
*Attorney, Agent, or Firm*—Robert H. Sproule; M. Norwood Cheairs

[57] ABSTRACT

A compound and a process for utilizing the compound to prevent the polymerization of vinyl aromatic compounds, such as styrene, during heating. The compound includes effective amounts of phenothiazine, 4-tert-butylcatechol and 2,6-dinitro-p-cresol respectively, as a polymerization inhibitor system in the presence of oxygen resulting in a less viscous polymer tar and in the effective inhibition of polymerization to temperatures as high as 150° C.

13 Claims, No Drawings

POLYMERIZATION CO-INHIBITORS FOR VINYL AROMATIC COMPOUNDS

BACKGROUND OF THE INVENTION

The present invention relates to a polymer inhibiting and polymer viscosity reducing composition and to a process for inhibiting the polymerization of readily polymerizable vinyl aromatic compounds and reducing the viscosity of polymers formed, during heating.

It is well known that vinyl aromatic compounds such as monomeric styrene, alpha-methyl styrene, and the like, polymerize readily and furthermore, that the rate of polymerization increases with increasing temperature. Inasmuch as vinyl aromatic compounds produced by common industrial methods contain impurities, these compounds must be subjected to separation and purification processes in order to be suitable for most types of further industrial use. Such separation and purification is generally accomplished by distillation techniques.

In order to prevent polymerization during distillation of vinyl aromatic compounds, various types of known polymerization inhibitors have been employed in connection with prior art distillation processes. For example, common inhibitors useful for inhibiting the polymerization of vinyl aromatic compounds under distillation conditions include 4-tert-butylcatechol (TBC) and hydroquinone. Additionally, sulfur has been widely employed as a polymerization inhibitor during the distillation of various vinyl aromatic compounds. However, while sulfur provides a reasonably effective inhibitor, its use in such distillation processes results in a highly significant disadvantage, namely, there is formed in the reboiler bottoms of the distillation column a valueless waste material highly contaminated with sulfur. This waste material furthermore represents a significant problem of pollution and waste removal.

Although many compounds are effective for inhibiting the polymerization of vinyl aromatic compounds under differing conditions, for example storage, only some of these compounds have proved to be any real utility for inhibiting vinyl aromatic polymerization under distillation conditions. One compound found effective for polymerization inhibition is 2,6-dinitro-p-cresol (DNPC) disclosed in U.S. Pat. No. 4,105,506 by Watson, incorporated herein by reference, where DNPC was found to be an effective inhibitor. It has been found, however, as the distillation temperature increases the effectiveness of DNPC decreases. In addition, it has been found that previously known polymerization inhibitors may be combined to achieve an inhibitory effect greater than either inhibitor alone. The synergistic effect of combining two known inhibitors was disclosed in U.S. Pat. No. 4,061,545 by Watson, incorporated herein by reference, wherein phenothiazine and 4-tert-butylcatechol were used together in the presence of oxygen as a polymerization inhibitor. It has been found, however, that when utilizing the phenothiazine/TBC mixture, a certain amount of polymerization of high molecular weight still occurs. This high molecular weight polymer results in a highly viscous polymer tar which decreases heat transfer within the reboiler areas of the distillation train and decreases recovery of the monomer trapped in the polymer tar. In addition, it has been found to be difficult to obtain complete dispersion of air throughout the distillation column thereby further reducing the effectiveness of the oxygen dependent phenothiazine/TBC inhibitor.

SUMMARY OF THE INVENTION

In order to overcome these problems there is provided in accordance with the present invention a composition for both inhibiting the polymerization of a readily polymerizable vinyl aromatic compound and for reducing the viscosity of polymer formed when the vinyl aromatic compound is subject to elevated temperatures, such as in a distillation apparatus, the composition comprising effective amounts of 2,6-dinitro-p-cresol, phenothiazine and 4-tert-butylcatechol respectively.

Also there is provided in accordance with the present invention, a process for inhibiting the polymerization of a readily polymerizable vinyl aromatic compound and reducing the viscosity of polymer formed when the vinyl aromatic compound is subject to elevated temperatures, the process comprising subjecting the vinyl aromatic compound to an inhibitory composition including effective amounts of 2,6-dinitro-p-cresol, 4-tert-butylcatechol and phenothiazine respectively, in the presence of oxygen.

It has been found that when DNPC is combined with TBC and phenothiazine, the molecular weight of the residual polymer tar is decreased resulting in a less viscous polymer tar and in an increased recovery of monomer. In addition, a more effective inhibitor is created resulting in decreased polymerization at temperatures up to 150° C.

According to the present process, the amount of polymerization occurring within the distillation apparatus is significantly reduced in comparison with conventionally employed methods. In addition, the amount of desired distillation products is increased in proportion to the decrease in the amount of polymer formed. Also, the rate of operation of a given distillation apparatus may be increased in proportion to the decrease in amount of polymer formation. Also, the rate of operation of a given distillation apparatus may be increased over and above the rate of operation of the same apparatus using conventional methods.

DETAILED DESCRIPTION OF THE PREFERRED EMBODIMENT

The present invention employs phenothiazine, 4-tert-butylcatechol, herein referred to as TBC, and 2,6-dinitro-p-cresol, herein referred to as DNPC, as a polymerization inhibitor composition during the distillation of vinyl aromatic compounds.

The vinyl aromatic compounds subject to the process of the present invention include styrene, alpha-methylstyrene, vinyltoluene, vinylnaphthalene, divinylbenzene and polyvinylbenzene; all the structural isomers and derivatives of the aforementioned compounds and mixtures thereof are also subject to the process of the present invention. The preferred vinyl aromatic compound subject to the present process is styrene.

One of the significant advantages of the present invention is the broad operative ranges of pressure and temperature and the reduction of unwanted polymerization. A particular advantage is the use of the polymer inhibitor to prevent unwanted polymerization at elevated temperatures in the distillation apparatus. Increasing the temperature in the apparatus has the advantages of a higher distillation rate, however, this increased temperature can cause a higher rate of polymerization which may be counterbalanced by the introduction of the inhibitor of the present invention.

According to one aspect of the process, the inhibitor is introduced into the distillation system by injection into the reboiler area of the distillation apparatus, or alternatively by injection into the incoming stream of vinyl aromatic compound to be purified. It is a feature of the present invention that the mode of introducing and metering the amount of polymerization inhibitor is considerably simplified due to the ease of metering the material, and due to the simplicity of the equipment necessary since the inhibitor is soluble in solvents compatible with the incoming feed.

The distillation technique of the process of the present invention is suitable for use in virtually any type of distillative separation of a readily polymerizable vinyl aromatic compound from a mixture wherein the vinyl aromatic compound is subject to temperatures above room temperature. Air or oxygen must be added to the system in order that the TBC/phenothiazine portion of the inhibitor works properly. It is also possible to pre-mix by dispersion or the like, the air or oxygen into the inhibitor system prior to adding the inhibitor. The oxygen employed in the present invention may be in the form of oxygen or an oxygen-containing gas. If an oxygen-containing gas is employed, the remaining constituents of the gas must be inert to the vinyl aromatic compound under the distillation conditions. The most useful, practical, and least expensive source of oxygen is air, which is preferred for the present invention. The amount of oxygen may vary widely but generally, it will be that amount found in air.

In one embodiment of the invention utilizing vacuum distillation in a three column distillation train such as the distillation train disclosed in U.S. Pat. No. 4,272,344 by Watson, incorporated herein by reference, it is necessary to add air only in the recycle column of the distillation train due to DNPC protection in the rest of the system. In the recycle or ethylbenzene column a more effective polymerization inhibitor is necessary due to the high temperatures up to 150° C. which are necessary in that column for more efficient energy recovery. Air is conveniently added into the recycle column reboiler or through the bottom of the recycle column itself. The air is dispersed throughout the column where it works in conjunction with the TBC and phenothiazine to inhibit the polymerization in the column. Complete dispersion of air throughout the column does not generally occur, therefore the presence of DNPC in the column works as a co-inhibitor at those locations where the effectiveness of the phenothiazine/TBC is diminished due to the absence of air. Therefore, the DNPC continues providing polymerization inhibition in those areas of the recycle column where there is an absence of air thereby providing an overall higher polymerization inhibition effectiveness than would have been achieved if only TBC/phenothiazine had been present by itself or in combination with other oxygen activated inhibitors. Surprisingly, it has been found that not only is DNPC compatible with the TBC/phenothiazine mixture, DNPC also works as effectively in the presence of air as in its absence. DNPC therefore provides additional inhibitor protection in those areas of the recycle column where there is effective air dispersion. It has been found, however, that when DNPC alone is used as an inhibitor in the presence of air, the DNPC is exhausted more rapidly. This may be due to the fact that more polymer free radicals are generated in the presence of air. Therefore, to maintain effective DNPC/air polymerization inhibition over an extended period of time it is necessary to add more DNPC inhibitor.

The amount of polymerization inhibition added may vary over wide ranges depending upon the conditions of distillation. Generally, the degree of inhibition is proportional to the amount of inhibitor added. In accordance with the present invention, it has been found that inhibitor concentrations based on the feed to the first distillation column generally between about 5 ppm and about 200 ppm phenothiazine in combination with about 100 ppm to about 200 ppm TBC and about 50 ppm to about 3000 ppm DNPC will generally have effective results depending primarily upon the temperature of the distillation mixture and the degree of inhibition desired. As the temperature increases and/or greater inhibition is required, then more inhibitor must be added. During distillation of the vinyl aromatic mixtures, the temperature of the reboiler is maintained from about 65° to about 150° C., preferably a temperature from about 90° C. to about 143° C. is maintained. Under such conditions in a distillation apparatus having a distillation zone containing from about 50 to 100 distillation stages, inhibitor concentrations based on the feed to the first distillation column of from about 25 to about 60 ppm phenothiazine in combination with about 20 ppm to about 50 ppm TBC and from about 100 ppm to about 600 ppm DNPC are preferred.

The polymerization inhibitor may be prepared by adding the compounds phenothiazine, TBC and DNPC together in random order at room temperature. In addition, these compounds may be injected separately into the distillation train along with the incoming feed, or through separate entry points. When utilized with the three column distillation train previously referred to, the TBC/phenothiazine may be introduced separately into the recycle column only; DNPC being introduced into the benzene-toluene or first column of the train.

The polymerization inhibitor of the present invention may be introduced into the distillation apparatus in any convenient manner which permits efficient distribution of the inhibitor throughout the apparatus. The inhibitor may be added to the incoming stream of feed material, into the reboiler area of the distillation train, or any other convenient location providing complete distribution of the inhibitor composition. Since the inhibitor is gradually depleted during operation, it is generally necessary to maintain the appropriate amount of inhibitor in the distillation apparatus by adding inhibitor during the course of the distillation process. Such addition may be carried out either on a generally continuous basis or it may consist of intermittently charging inhibitor into the distillation system if the concentration of inhibitor is to be maintained above the minimum required level.

Use of the polymerization inhibitor of the present invention enables the distillation apparatus to operate at an increased rate as opposed to prior art processes because the inhibitor of the present invention has greater inhibitive effects than conventional inhibitors and thus will permit higher distillation temperatures at higher pressures.

It should be understood that in spite of the effectiveness of the polymerization inhibitor, a small amount of polymerization of the vinyl aromatic compound will still occur, approximately up to 2% at 115° C. and 4% at 150° C. by weight of vinyl aromatic compound. When the process of the present invention is utilized, the bottoms material including the polymer tar which accumulates during the distillation process can be drawn off to undergo further separation of any monomer trapped therein. A significant advantage of the present invention is the reduction in molecular weight of the polymer tar formed in the reboiler area. Reduction in molecular weight and the consequent reduction in viscosity not only allows for a more efficient heat transfer within the reboiler, but also allows for easier and more complete separation of any monomer remaining in the polymer tar. It is believed that DNPC, in addition to its inhibitory characteristics, also acts as a chain transfer agent to decrease the size of the polymer chains formed and therefore the molecular weight of the polymer tar. Since DNPC works effectively both in the presence and absence of air, its effectiveness as a chain transfer agent is utilized throughout a distillation train. After separation of the monomer, the remaining bottoms material is drawn off and utilized for its heating value or for reprocessing as the amount of sulfur contamination from phenothiazine is relatively inconsequential; this represents another significant advantage in comparison with conventional processes for distillation of vinyl aromatic compounds which employ sulfur as the polymerization inhibitor or sulfur in combination with other chemical polymerization inhibitors.

Upon recovery of the distillation product obtained from the process of the present invention, it is found that a higher percentage of the pure readily polymerizable vinyl aromatic compound is recovered in an unpolymerized state, and that the inhibitor employed does not detract from the ability of the recovered monomer to undergo subsequent polymerization. Furthermore, it has been noted that the polymeric products which are formed during the distillation process of the invention are of such a character that there is less fouling or plugging of the apparatus as compared with many conventional inhibitors. In order to more fully describe the present invention, the following examples are presented which are intended to be illustrative, and not in any sense limitative of the invention.

EXAMPLE 1

Two 100 ml reaction flasks were prepared. A first (1) was charged with 25 grams styrene to which was added 100 ppm DNPC, 50 ppm phenothiazine, 40 ppm TBC; a second (2) flask was charged with 25 grams styrene containing approximately 200 ppm DNPC. Each of these flasks was fitted with a magnetic stirrer and septum closures and heated in a stirred oil bath to 138° C., plus or minus 1° C., and carried to approximately 5% polymerization. Samples were removed periodically from each of the reaction flasks through a hypodermic syringe and tested for turbididy with methanol. The polymer was then concentrated on a rotary evaporator and prepared for gel permeation chromotography analysis. The following results were obtained:

|  | Flask 1 | Flask 2 |
| --- | --- | --- |
| % polymerization | 2.54 | 5.27 |
| mn | 36,000 | 31,000 |
| molecular weight | 158,000 | 170,000 |
| density | 4.4 | 5.3 |

This example illustrates the excellent chain transfer qualities of the DNPC in combination with the phenothiazine and TBC to reduce the molecular weight of the polymer formed.

EXAMPLE 2

Two 100 ml reaction flasks were prepared. A first (1) is charged with 25 grams styrene to which was added 100 ppm DNPC, 50 ppm phenothiazine and 40 ppm TBC; a second (2) was charged with 25 grams of styrene containing 200 ppm DNPC. Each of the flasks was fitted with a magnetic stirrer and septum closures and heated in a stirred oil bath to 126° C. plus or minus 1° C. The first flask was purged with 1-2 ml/min of air run beneath the liquid surface during the period of distillation. Flask 2, on the other hand, was purged with a nitrogen blanket. After two hours the samples in flask 1 and 2 were tested for the degree of styrene polymerization by determining the change in refractive index of each sample; as a check on this method, occasionally the monomer was stripped off and the remaining polymer weighed. A final polymer yield of 0.42% resulted in flask 1, whereas a polymer yield of 3.10% resulted in flask 2.

EXAMPLE 3

The procedure of Example 2 was followed utilizing an oil bath temperature of 138° C., plus or minus 1° C. The following results were obtained: Flask 1 resulted in a polymer yield of 3.18%, whereas flask 2 resulted in a polymer yield of 11.2%.

EXAMPLE 4

The procedure of Example 2 was followed, however, the amounts of phenothiazine and TBC were doubled, thereby resulting in a concentration of phenothiazine of 100 ppm and a concentration of TBC of 80 ppm. An oil bath temperature of 138° C., plus or minus 1° C., was used. The following results were obtained: Flask 1 a polymer yield of 2.16% resulted, whereas in flask 2, containing the DNPC only, a polymer yield of 14.3% resulted.

COMPARISON EXAMPLE 4

A 100 ml reaction flask was charged with 25 grams styrene to which was added 100 ppm phenothiazine and 80 ppm TBC. The flask was heated with a magnetic stirrer and septum closure and heated in a stirred oil bath to 138° C., plus or minus 1° C., under an air purge of 1-2 ml/min. After two hours the sample was tested for polymerization resulting in a polymer yield of 11.5%, thereby confirming that DNPC is a necessary component of the phenothiazine/TBC mixture to maintain effective polymerization inhibition.

Accordingly, therefore, it is observed from the foregoing data that DNPC alone or phenothiazine/TBC alone, is not capable of providing the degree of inhibition observed when the three are employed together; that is, phenothiazine/TBC employed together with DNPC as co-inhibitors for preventing polymerization of vinyl aromatic compounds. Furthermore, it is to be observed from the foregoing data that the DNPC, phenothiazine, TBC composition inhibitor showed an effective degree of inhibition at significantly elevated temperatures.

While the present invention has been described in terms of various embodiments and illustrated by numerous examples, the person of ordinary skill in the art will appreciate that various modifications, substitutions, omissions and changes may be made without departing from the spirit thereof.

We claim:

1. A composition for inhibiting polymerization of vinyl aromatic compounds and for reducing the viscosity of polymer formed, comprising:
   (a) an effective amount of 2,6-dinitro-p-cresol;
   (b) an effective amount of phenothiazine; and
   (c) an effective amount of 4-tert-butylcatechol.

2. The composition of claim 1 wherein the vinyl aromatic compound is selected from the group consisting of styrene, alpha-methylstyrene, vinyltoluene, vinylnaphthalene, divinylbenzene, and structural isomers, derivatives and mixtures thereof.

3. The composition of claim 1 wherein the vinyl aromatic compound is styrene.

4. The composition of claim 1 wherein:
   (a) the 2,6-dinitro-p-cresol is present in an amount from about 50 ppm to about 3000 ppm;
   (b) the phenothiazine is present in an amount from about 5 ppm to about 200 ppm; and
   (c) the 4-tert-butylcatechol is present in an amount from about 100 ppm to about 200 ppm.

5. The composition of claim 1 wherein:
   (a) the 2,6-dinitro-p-cresol is present in the amount from about 100 ppm to about 600 ppm;
   (b) the phenothiazine is present in the amount from about 20 ppm to about 60 ppm; and
   (c) the 4-tert-butylcatechol is present in an amount from about 20 ppm to about 50 ppm.

6. A process for inhibiting the polymerization of a vinyl aromatic compound and for reducing the viscosity of polymer formed, said process comprising subjecting the vinyl aromatic compound when heated to an inhibitory composition including effective amounts of 2,6-dinitro-p-cresol, 4-tert-butylcatechol, and phenothiazine respectively, in the presence of oxygen.

7. The process of claim 6 wherein the vinyl aromatic compound is selected from the group consisting of styrene, alpha-methylstyrene, vinyltoluene, vinylnaphthalene, divinylbenzene, and structural isomers, derivatives and mixtures thereof.

8. The process of claim 6 wherein the vinyl aromatic compound is styrene.

9. The process of claim 6 wherein:
   (a) the effective amount of 2,6-dinitro-p-cresol is from about 50 ppm to about 3000 ppm;
   (b) the effective amount of phenothiazine is from about 5 ppm to about 200 ppm; and
   (c) the effective amount of 4-tert-butylcatechol is from about 1 ppm to about 200 ppm.

10. The process of claim 6 wherein the heating of the vinyl aromatic compound occurs during distillation of said compound.

11. The process of claim 6 wherein the inhibitory composition is subjected to oxygen only in that portion of a distillation train having the highest temperature.

12. The process of claim 6 wherein the vinyl aromatic compound is heated to a temperature up to 150° C.

13. The process of claim 6 wherein the composition of claim 1 is continuously added to the vinyl aromatic compound.

* * * * *